United States Patent [19]
Wessel

[11] Patent Number: 5,654,493
[45] Date of Patent: Aug. 5, 1997

[54] PROCESS FOR PREPARING 4-BROMOPHENYL ALKYL ETHERS

[75] Inventor: Thomas Wessel, Frankfurt, Germany

[73] Assignee: Hoechst Aktiengesellschaft, Germany

[21] Appl. No.: 702,812

[22] Filed: Aug. 26, 1996

[30] Foreign Application Priority Data

Aug. 26, 1995 [DE] Germany .................. 195 31 408.5

[51] Int. Cl.$^6$ .................................. C07C 41/24
[52] U.S. Cl. ........................................ 568/656
[58] Field of Search .............................. 568/656

[56] References Cited

FOREIGN PATENT DOCUMENTS

| 0429975 | 6/1991 | European Pat. Off. . |
| 3742515 | 7/1988 | Germany . |

OTHER PUBLICATIONS

Reverdin, F., et al, *Chem. Ber* 32:152–167 (1899).
Bodroux, F., *C. R. Hebd. Seances Acad., Sci.* 136:377–379.
Slotta, K. H., et al, *Chem Ber.* 63:3029–3037 (1930).
A. Roedig in *Houben–Weyl–Muller*, "Methoden der Organischen Chemie" [Methods in Organic Chemistry], vol. 4, 1960, pp. 246 and 269.
Olah, G. A., et al, *Synthesis:*868:870 (1986).
Choudary, B. M., et al, *Synlett*: 450 (1994).

*Primary Examiner*—Samuel Barts
*Attorney, Agent, or Firm*—Connolly and Hutz

[57] ABSTRACT

The present invention relates to a process for preparing 4-bromophenyl alkyl ethers by reacting phenyl alkyl ethers with bromine in a water-miscible solvent in the presence of an oxidizing agent which is able to oxidize hydrogen bromide to bromine.

10 Claims, No Drawings

PROCESS FOR PREPARING 4-BROMOPHENYL ALKYL ETHERS

The present invention relates to a process for preparing 4-bromophenyl alkyl ethers by bromination of the corresponding alkyl phenyl ethers with bromine in the presence of an oxidizing agent.

4-Bromophenyl alkyl ethers are very widely used as valuable synthetic building blocks, e.g. as intermediates for insecticides, for preparing medicaments and as additives in the plastics and chewing gum sectors.

As is known, these compounds are prepared by bromination of the corresponding alkyl phenyl ethers, alternative syntheses, such as bromine-Sandmeyer reactions of the correspondingly substituted anilines being of minor importance (see, e.g. Chem. Ber., 32 (1899) 160).

Preferred solvents in the bromination of alkyl phenyl ethers are frequently inert chlorinated hydrocarbons, such as, inter alia: dichloroethane, methylene chloride and carbon tetrachloride or carbon disulfide, which are hazardous to health, toxic or even carcinogenic, and their use in a synthesis performed on the industrial scale is of concern from ecological and workers' health aspects.

Thus G. A. Olah et al. (Synthesis 1986, pp. 868–870) describe brominations of anisole and phenetole with bromodimethylsulfonium bromides in methylene chloride as solvent. Processes for preparing bromophenols and derivatives thereof in the presence of liquid organic esters as solvent, as mentioned in DE-A 37 42 515, when converted to the industrial scale, for safety reasons, likewise require complex equipment, in particular to protect plants against fire and explosions.

Brominations of anisole or phenetole in acetic acid are likewise known, but have hitherto been of only minor importance, since, inter alia, to suppress side reactions, such as ether cleavage, in the bromination of phenol ethers, the addition of a hydrogen-bromide-binding agent, such as sodium acetate or calcium carbonate, or the expulsion of the resulting HBr is frequently necessary (cf. A. Roedig in Houben-Weyl-Müller, Methoden der Organischen Chemie [Methods in Organic Chemistry], Volume V/4 p. 246, p. 269, Stuttgart 1960). Thus, A. Roedig describes the bromination of anisole in glacial acetic acid with vaporous bromine in a current of air, 1.05 mol of bromine ($Br_2$) being used per mole of anisole. The yield achieved is 83% of theory. In these processes, 1 mol of hydrogen bromide is inevitably produced per mole of bromophenyl alkyl ether formed, which hydrogen bromide is dissolved in the filtrate or must be scrubbed out of the exhaust air. Further processes described for the bromination of anisole in glacial acetic acid (cf. Chem. Ber., 63 (1930) 3029 and C. R. Hebd. Seances Acad. Sci., 136 (1903) 378) or of phenetole in glacial acetic acid (ibid. 136 (1903) 378) do not represent an improvement with respect to the production of hydrogen bromide, since in these preparation processes, significantly less than half of the bromine introduced is utilized.

Bromination reactions on aromatic compounds in which the hydrogen bromide produced from the bromine is reconverted to bromine by adding an oxidizing agent are known. Thus, EP-B1 429 975 describes the preparation of dibrominated diphenyl ethers with bromine in the presence of oxidizing agent in a 2-phase system, the reaction being carried out in water-immiscible organic solvents. Preferred solvents in this case are 1,2-dichloroethane, methylene chloride or methylene bromide, whose use is, as already stated, of concern from ecological and workers' health aspects.

In addition, B. M. Choudary et al. (Synlett 1994, p. 450) describe the regioselective oxybromination, inter alia, of anisole in the presence of ammonium molybdate catalysts. Although the solvent used in this case is the ecologically harmless acetic acid, the use of a heavy metal catalyst causes considerable disposal problems for this process when it is converted to an industrial scale, and in addition using a non-regenerable catalyst represents a not insignificant cost disadvantage. Owing to the use of potassium bromide large amounts of inorganic salts are produced, in addition, in this process, which must be removed from process wastewaters in a labor- and energy-intensive manner.

The object of the present invention is therefore to provide a process for preparing 4-bromophenyl alkyl ethers which is improved from ecological and workers' health aspects, decreases wastewater pollution and avoids the use of chlorinated hydrocarbons and which gives highly pure products in high yield in a technically simple manner.

The present invention thus relates to a process for preparing compounds of the formula I

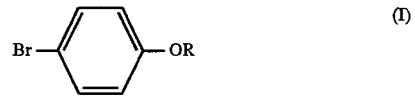

in which R is an alkyl group, by reacting a compound of the formula II

in which R is defined as specified above, with bromine in a water-miscible solvent, which comprises carrying out the process in the presence of an oxidizing agent which is able to oxidize hydrogen bromide to bromine.

Alkyl groups which are R can be straight-chain or branched and preferably have one to six carbon atoms. Examples are methyl, ethyl, n-propyl, i-propyl, n-butyl, i-butyl, sec-butyl and tert-butyl. Particularly preferably, R is methyl and ethyl.

Suitable oxidizing agents which are able to oxidize hydrogen bromide to bromine are, in particular, those which do not participate in side reactions with the compounds of the formula I nor with the compounds of the formula II. Preferred oxidizing agents are manganese dioxide, cerium(IV) salts, alkali metal bromates and peroxy compounds. Particularly preferred oxidizing agents are peroxy compounds, which are to be taken to include hydrogen peroxide and its inorganic and organic derivatives in which one or both hydrogen atoms are replaced by covalently bound radicals or by ionically bound cations.

Suitable peroxy compounds are, for example, sodium peroxide and barium peroxide and their hydrates; butyl hydroperoxide; peroxyformic acid, peroxyacetic acid, peroxypropionic acid, peroxylauric acid, peroxybenzoic acid, m-chloroperoxybenzoic acid and their alkali metal salts and alkaline earth metal salts; the so-called alkali metal perborates and alkali metal percarbonates, such as sodium perborate and sodium percarbonate; and peroxomonosulfuric acid, peroxodisulfuric acid and their alkali metal salts and ammonium salts.

A particularly preferred oxidizing agent is hydrogen peroxide, which is advantageously used in the form of commercial aqueous solutions in the concentration range from 20 to 50% by weight.

The amount of oxidizing agent required depends, in particular, on the reaction procedure.

An excess of oxidizing agent is frequently used in order to achieve a complete and rapid reoxidation. If hydrogen peroxide is used as oxidizing agent, a 0.5 times to equimolar molar amount, based on the compound of the formula II, can be expedient, 0.62 to 0.72 mol of hydrogen peroxide, based on the compound of the formula II, being particularly preferred.

In the process of the invention, bromine is generally used in amounts of 0.5 to 0.6 mol ($Br_2$) per mole of compound of the formula II. Particular preference is given to 0.52 to 0.56 mol per mole of compound of the formula II, depending on how the process of the invention is carried out.

The process of the invention is carried out in a water-miscible solvent or in mixtures of water-miscible solvents. Examples are water-miscible carboxylic acids or water itself. In particular when the oxidizing agent is used in the form of an aqueous solution, the use of water-miscible carboxylic acids as solvents is preferred. Examples of such carboxylic acids are formic acid, acetic acid and propionic acid. A very particularly preferred solvent is acetic acid.

The process of the invention is carried out, in particular, at temperatures between 0° C. and the boiling point of the reaction mixture. Preferred temperatures are 20° to 50° C., particularly preferred temperatures are 30° to 40° C.

In one embodiment of the process of the invention, the compound of the formula II is charged together with the solvent and the oxidizing agent and the bromine is added. However, the compound of the formula II can alternatively be charged together with the solvent and then first bromine and then oxidizing agent can be added. However, bromine and oxidizing agent can also be added together.

The compound of the formula I can be isolated by conventional work-up methods, which depend on the solubility of the product in the solvent used and its fixed point. Conventional work-up methods in this case are chromatography, filtration, phase separation, centrifugation or distillation at atmospheric pressure or at reduced pressure. Work-up by distillation is, in particular, the method of choice in the case of lower 4-bromophenyl alkyl ethers.

EXAMPLES

1. Bromination of phenetole in acetic acid

In a 1 l multinecked flask equipped with a stirrer, 840 g of glacial acetic acid (800 ml) and 123 g of phenetole (99% pure according to GC, equivalent to 1 mol) are mixed together at room temperature with addition of 65 g of 35% strength aqueous hydrogen peroxide solution (equivalent to 0.67 mol of $H_2O_2$). Over a period of approximately 45 min, 86.5 g of bromine (equivalent to 0.54 mol of $Br_2$) are then added in such a manner that the internal temperature does not exceed 30°–35° C. External cooling is performed using a waterbath. After bromine addition has been completed, the mixture is stirred for a further 15 min and the acetic acid is then distilled off at a reduced pressure of 165–150 mbar via a distillation bridge using a packed column (20 cm in height, packing: 6 mm Raschig rings).

The aqueous acetic acid distilled off contains 8 g of 4-bromophenetole, corresponding to 4% of theory.

After the acetic acid has been distilled out, the product is distilled directly at a reduced pressure of 40–45 mbar, 4-bromophenetole boiling at a constant temperature of 124°–127° C.

181 g of 4-bromophenetole are obtained as a colorless oil, corresponding to 89.7% of theory.

| Purity (GC): | 0.53% | 2-bromophenetole |
| --- | --- | --- |
| | 98.64% | 4-bromophenetole |
| | 0.58% | 2,4-dibromophenetole |

2. Bromination of phenetole in acetic acid

If the procedure is followed as in Example 1, the product distillation, however, being performed additionally by a reflux divider (reflux ratio 10:1), the content of 2,4-dibromophenetole can be further markedly decreased:

| Purity (GC): | 0.49% | 2-bromophenetole |
| --- | --- | --- |
| | 98.86% | 4-bromophenetole |
| | 0.19% | 2,4-dibromophenetole |

3. Bromination of anisole in acetic acid

In a 1 l multinecked flask equipped with a stirrer, 525 g of acetic acid (500 ml) and 109 g of anisole (99% pure according to GC, equivalent to 1 mol) are mixed at room temperature with 65 g of 35% strength aqueous hydrogen peroxide solution (equivalent to 0.67 mol of $H_2O_2$).

Over a period of approximately 1 h, 84 g of bromine (0.525 mol of $Br_2$) are then added in such a manner that the internal temperature does not exceed 35° C. After the addition of bromine, the mixture is further stirred for 30 min and the acetic acid is then distilled off at a reduced pressure of 157–167 mbar via a distillation bridge using a packed column (height: 20 cm, 6 mm Raschig rings).

The acetic acid distilled off contains 6.3 g of 4-bromoanisole, corresponding to 3.5% of theory.

After the acetic acid has been distilled out, the product is distilled directly at a reduced pressure of 48–53 mbar, 4-bromoanisole boiling at a constant temperature of 117°–119° C.

165 g of 4-bromoanisole are obtained in this manner as a colorless oil, corresponding to 88.2% of theory.

| Purity (GC): | 0% | 2-bromoanisole |
| --- | --- | --- |
| | 99.6% | 4-bromoanisole |
| | 0.33% | 2,4-dibromoanisole |

I claim:

1. A process for preparing compounds of the formula I

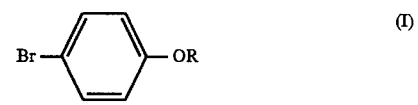

in which R is an alkyl group, by reacting a compound of the formula II

in which R is defined as specified above, with bromine in a water-miscible solvent, which comprises carrying out the process in the presence of an oxidizing agent which is able to oxidize hydrogen bromide to bromine.

2. The process as claimed in claim 1, wherein R is ($C_1$–$C_6$)-alkyl.

3. The process as claimed in claim 1, wherein R is methyl or ethyl.

4. The process as claimed in claim 1, wherein the oxidizing agent used is manganese dioxide, a cerium(IV) salt, an alkali metal bromate or a peroxy compound.

5. The process as claimed in claim 1, wherein the oxidizing agent used is hydrogen peroxide.

6. The process as claimed in claim 1, wherein the oxidizing agent used is hydrogen peroxide in amounts of 0.62 to 0.72 mol per mole of compound of the formula II.

7. The process as claimed in claim 1, wherein the solvent used is a water-miscible carboxylic acid.

8. The process as claimed in claim 1, wherein the solvent used is acetic acid.

9. The process as claimed in claim 1, wherein bromine is used in amounts of 0.5 to 0.6 mol ($Br_2$) per mole of compound of the formula II.

10. The process as claimed in claim 1, wherein it is carried out at temperatures of 20° to 50° C.

* * * * *